United States Patent
Hsieh et al.

(10) Patent No.: US 6,989,273 B2
(45) Date of Patent: Jan. 24, 2006

(54) LIGHT EMISSIVE IRIDIUM (III) COMPLEXES

(75) Inventors: Bing R. Hsieh, Webster, NY (US); Travis P. S. Thoms, San Lorenzo, CA (US); Jian Ping Chen, San Jose, CA (US)

(73) Assignee: Canon Kabushiki Kaisha, Tokyo (JP)

( * ) Notice: Subject to any disclaimer, the term of this patent is extended or adjusted under 35 U.S.C. 154(b) by 435 days.

(21) Appl. No.: 10/067,797

(22) Filed: Feb. 8, 2002

(65) Prior Publication Data

US 2003/0162299 A1  Aug. 28, 2003

(51) Int. Cl.
*G01N 33/00*  (2006.01)

(52) U.S. Cl. .................. 436/84; 428/690; 428/917; 428/212

(58) Field of Classification Search ................. 436/84; 428/690, 917, 212
See application file for complete search history.

(56) References Cited

U.S. PATENT DOCUMENTS

| | | | |
|---|---|---|---|
| 4,720,432 A | | 1/1988 | VanSlyke et al. |
| 4,954,414 A | | 9/1990 | Adair et al. |
| 5,585,279 A | | 12/1996 | Davidson |
| 5,660,991 A | | 8/1997 | Lakowicz et al. |
| 5,822,137 A | | 10/1998 | Abul-Haj et al. |
| 5,874,803 A | | 2/1999 | Garbuzov et al. |
| 5,958,783 A | * | 9/1999 | Josel et al. .................... 436/84 |
| 5,981,286 A | | 11/1999 | Herrmann et al. |
| 6,018,065 A | | 1/2000 | Baum et al. |
| 6,048,630 A | | 4/2000 | Burrows et al. |
| 6,126,996 A | | 10/2000 | Kirlin et al. |
| 6,166,489 A | | 12/2000 | Thompson et al. |
| 6,215,245 B1 | | 4/2001 | Mori |
| 6,565,994 B2 | * | 5/2003 | Igarashi ....................... 428/690 |
| 6,660,410 B2 | * | 12/2003 | Hosokawa .................. 428/690 |
| 6,660,631 B1 | * | 12/2003 | Marsh ........................ 438/680 |
| 6,670,645 B2 | * | 12/2003 | Grushin et al. ................ 257/98 |

FOREIGN PATENT DOCUMENTS

| | | |
|---|---|---|
| WO | WO 01/39234 | 5/2001 |
| WO | WO 01/41512 | 6/2001 |

OTHER PUBLICATIONS

C. M. Flynn, Jr., et al., "Synthesis and Luminescence of the Tris(2,2'-bipyridine Iridium (III) Ion", J. Amer. Chem Soc., Mar. 20, 1974, vol. 96, No. 6, pp. 1959-1960.

* cited by examiner

*Primary Examiner*—Jill Warden
(74) *Attorney, Agent, or Firm*—Fitzpatrick, Cella, Harper & Scinto

(57) ABSTRACT

Emissive iridium (III) complexes suitable for use in an emissive layer of an OLED and having the structure:

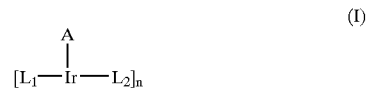

(I)

wherein $L_1$ and $L_2$ are heteroaromatic ligands having a carbon atom covalently bonded to the iridium atom and a nitrogen atom complexed to the iridium atom, and wherein A comprises n heteroaromatic ligand groups defined as for $L_1$ and $L_2$, bonding to the respective n iridium atoms, and n is 2–12.

9 Claims, 1 Drawing Sheet

LIGHT EMISSIVE IRIDIUM (III) COMPLEXES

BACKGROUND OF THE INVENTION

1. Field of the Invention

The present invention is directed to iridium (III) complexes used as emissive materials in electroluminescent (EL) devices, and in particular organic light emitting devices (OLEDs).

2. Description of the Related Art

OLEDs are typically comprised of at least a layer of emissive material sandwiched between an anode, typically comprised of a transparent conductor such as indium-tin oxide, and a cathode, typically a low work-function metal, such as magnesium, calcium, aluminum, or the alloys thereof, with other metals. When a bias is applied across the electrodes, positive charges (holes) and negative charges (electrons) are respectively injected from the anode and cathode into the emissive layer. The holes and the electrons form excitons in the emissive layer to emit light.

Many metal-ligand complexes have been used in the emissive layers of OLEDs, including blue light emitting layers made from trivalent metal quinolate complexes, Schiff base divalent metal complexes, metal acetylacetonate complexes, metal bidentate ligand complexes, and rare earth mixed chelates, as well as red light emitting layers made from luminescent iridium (I), rhodium (I), and platinum (II) dithiolate complexes. These metal-complexes can be used in conjunction with organic dyes.

The synthesis of a luminescent tris(2,2'-bipyridine)iridium(III) ion is disclosed in Journal of the American Chemical Society, Vol. 96, No. 6, 1959–60 (1974).

International Application WO 01/41512 discloses metal complexes suitable for use in OLEDs, having a metal species associated with three bidentate ligands. The metal species is coordinated with an sp2 hybridized carbon and a heteroatom of the ligands.

SUMMARY OF THE INVENTION

The invention is directed to neutral iridium(III) complexes suitable for use in an emissive layer of an OLED and having the structure:

(I)

wherein $L_1$ and $L_2$ are heteroaromatic ligands having a carbon atom covalently bonded to the iridium atom and a nitrogen atom complexed to the iridium atom, and wherein A comprises n heteroaromatic ligand groups defined as for $L_1$ and $L_2$, bonding to the respective n iridium atoms and n is equal to or greater than two. In preferred embodiments $L_1$ and $L_2$ are independently selected from among:

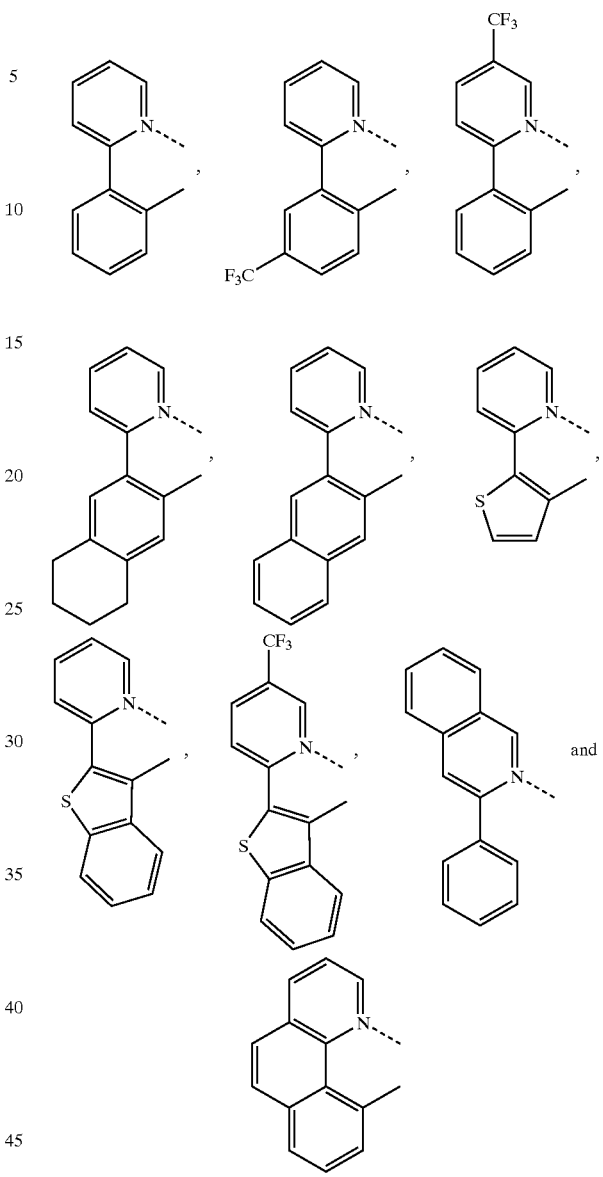

The carbon trifluoride substituents shown in the examples above are preferred. However, those of skill in the art will recognize that any ring in the foregoing structures maybe substituted with other groups.

In the case where n=2, Formula (I) may, in preferred embodiments, be written as:

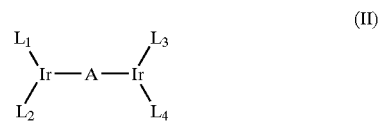
(II)

where A is a dimeric ligand, L'-R-L", where R is hydrocarbon, and L' and L", which may be the same or different, are heteroaromatic ligands having a carbon atom covalently bonded to the iridium atom and a nitrogen atom complexed to the iridium atom. Each of $L_1$ through $L_4$ in Formula (III), which may be the same or different, is a ligand having a carbon atom covalently bonded to the iridium atom.

Examples of dimeric ligands L'-R-L" include:

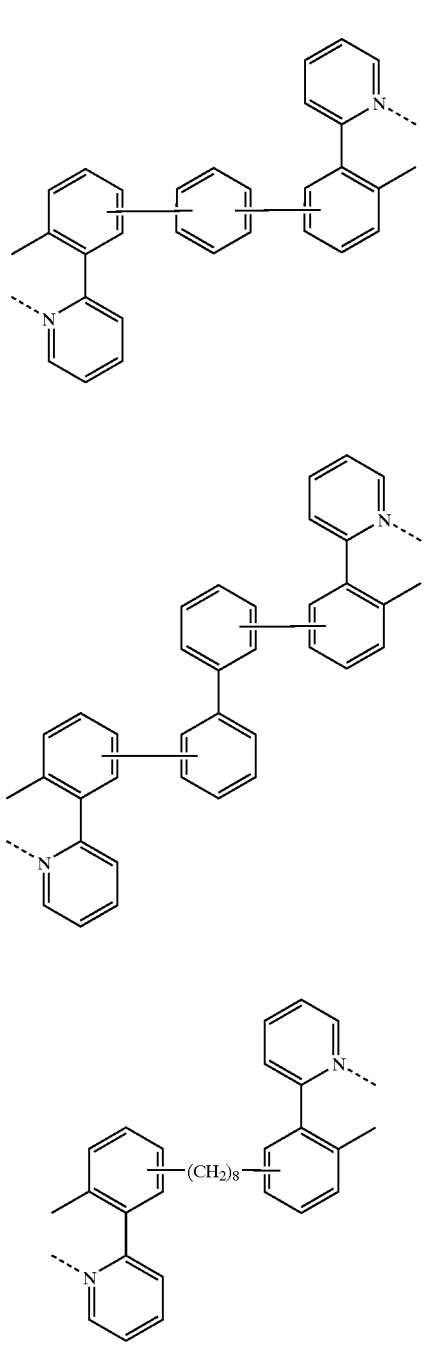

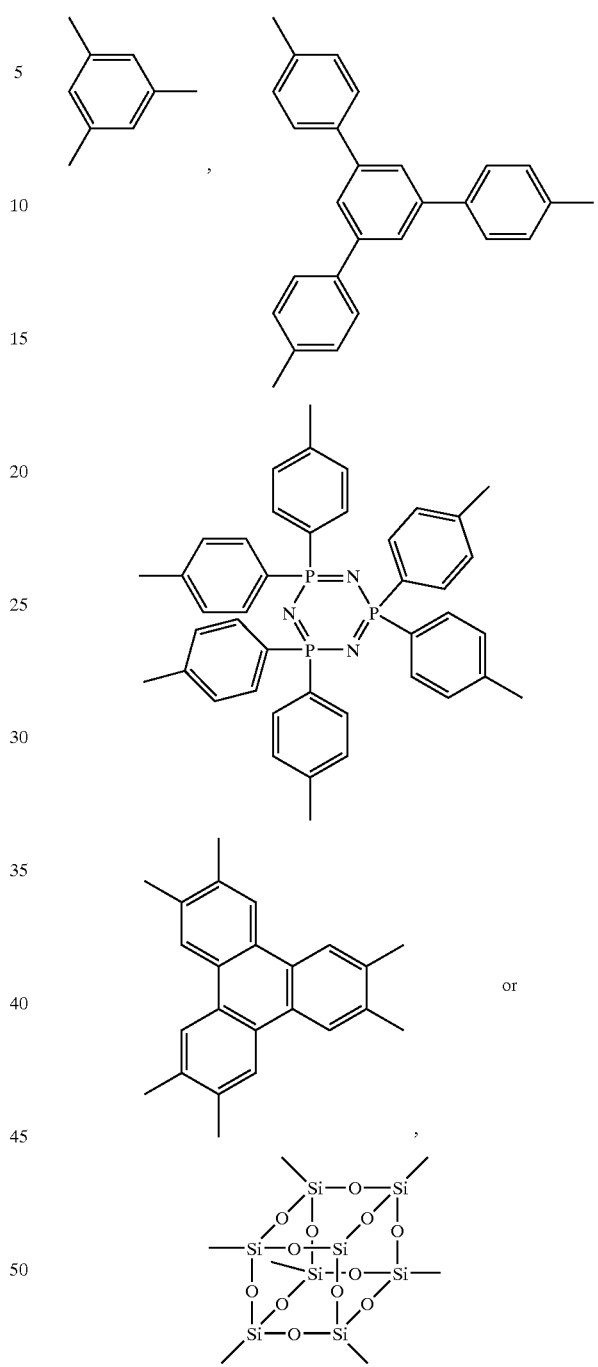

In the case where n is greater than or equal to 3, A can be written as Core-Rn-L'n, and Formula (I) may be written:

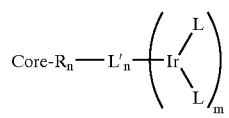

(III)

where "core" is a m-valent moiety such as:

Rn is hydrocarbon, preferably aromatic or alkyl, and L'n is a ligand having a carbon covalently bonded to the iridium atom, and a heteroatom complexed to the iridium atom. Ligands L, which may be the same or different each have a carbon atom covalently bonded to the respective iridium atom, such as, without limitation, 2-phenyl pyridine.

The iridium(III) complexes according to the invention exhibit unique photoemissions compared to the symmetric, ionic tris(2,2'-bipyridine)iridium(III) complexes known in the art. The core moiety "A" bonding multiple iridium-bonded groups provides unique properties as compared to prior art complexes consisting of a single iridium atom and three bidentate ligands.

This brief summary has been provided so that the nature of the invention may be understood quickly. A more complete understanding of the invention can be obtained by reference to the following detailed description of the preferred embodiments thereof in connection with the attached drawing.

DETAILED DESCRIPTION OF THE PREFERRED EMBODIMENTS

Figure 1:
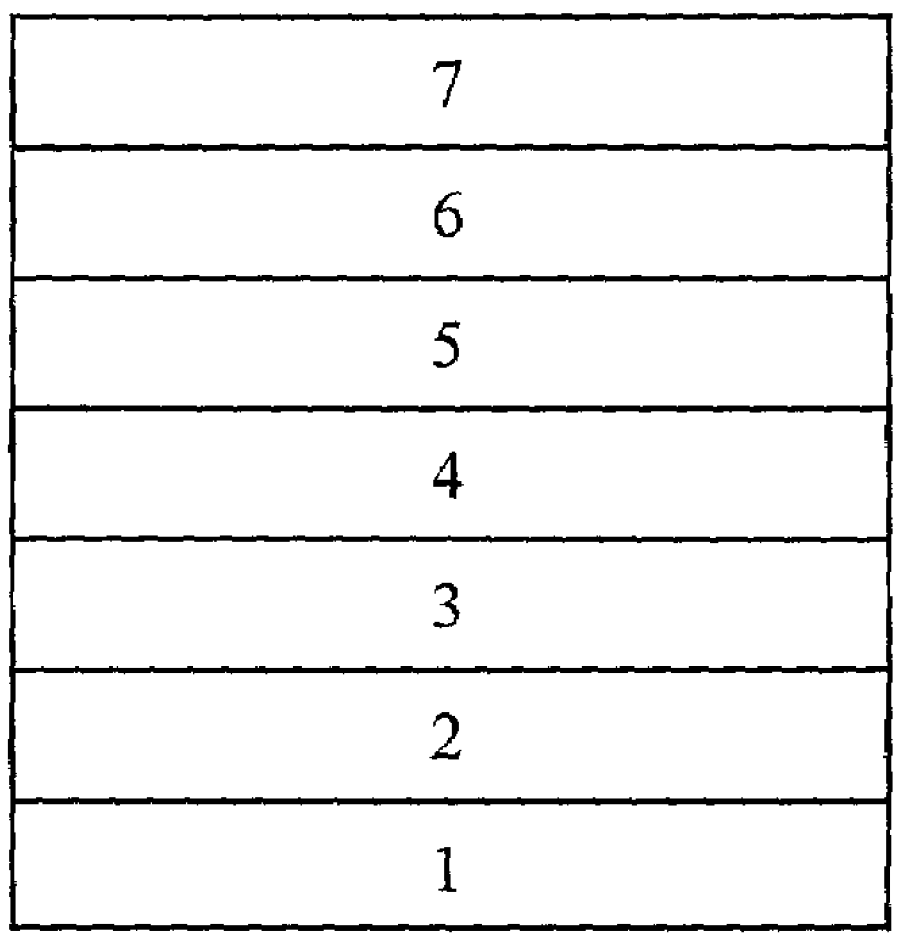
FIG. 1 is a cross-sectional view of an EL device according to the invention.

Luminescence observed in OLEDs may be fluorescent or phosphorescent. Fluorescence is understood to mean luminescent emission occurring only during the period during which an excitation (such as a driving voltage) is applied, and is created mostly, if not exclusively, by relaxation from the singlet state. Phosphorescence is luminescent emission which persists after the period of excitation. Phosphorescence involves photons created by relaxation from triplet states. Of particular importance in the present invention is triplet-enhanced fluorescent emissions.

The internal efficiency of many OLED emissive materials is limited by the fact that singlet and triplet excited states are produced in these materials at a ratio of 1:3, but emission typically only involves singlet relaxation. Accordingly, efficiency can only approach a theoretical maximum of 25%. It is believed that the carbon-iridium covalent bond in the complexes according to the invention causes spin orbital coupling such that the triplet state has quantum mechanical properties similar to the singlet state and therefore relaxation from the triplet state in these complexes contributes to emissions. In this manner, theoretical efficiencies greater than 25% can be obtained.

The examples below exhibit yellow phosphorescent emissions, although other pure colors can be obtained by incorporating other conjugated groups into the complexes.

EXAMPLE 1

To a round-flask were added iridium(III)chloride (0.298 g, 1 mmol), 2-phenylpyridine (0.62 g, 4 mmol), 30 mL of 2-ethoxyethanol, and 10 mL of water. The mixture was fluxed under $N_2$ overnight. After cooling, the solid was filtrated and washed with a small amount of ethanol and acetone. The product was dissolved in dichloromethane and filtrated. Thereafter, a mixture of hexanes and toluene was added to the filtrate, and the solution was concentrated. The intermediate product tetrakis(2-phenylpyridine-$C^2$,N')diiridium $(IrPPy_2Cl)_2$ (structure shown below) was collected by filtration as yellow crystals.

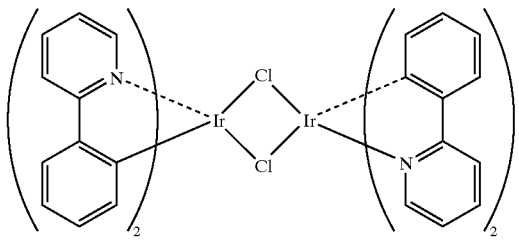

To a round-flask were added the above $(IrPPy_2Cl)_2$ (1.07 g, 1 mmol), 2,4-pentanedione (0.26 g, 2.5 mmol), sodium carbonate (1.2 g), and 20 mL of 2-ethoxyethanol. The mixture was fluxed under $N_2$ overnight. After cooling, the solid was filtrated and washed with a small amount of ether and hexanes. The intermediate product Iridium(III) bis(2-phenylpyridinato-N,$C^2$)acetylacetonate (structure shown below) was purified by silica-gel chromatography using dichloromethane as an eluent.

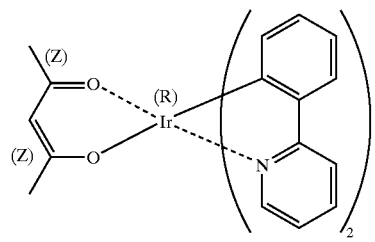

To a round-flask were added iridium(III) bis(2-phenylpyridinato-N,$C^2$)acetylacetonate (0.3 g, 0.5 mmol), benzoquinoline (0.09 g, 0.5 mmol) and 10 mL of glycerol. The mixture was fluxed under $N_2$ overnight. After cooling, water and dichloromethane were added to the mixture. The product Iridium(III) bis(2-phenylpyridinato-N,$C^2$)benzoquinoline (structure shown below) was extracted with dichloromethane and washed with water, purified by chromatography using dichloromethane as an eluent. Yield: 0.12 g (45%). Td (5% weight loss)=350° C. The compound exhibited a yellow phosphorescent luminescence.

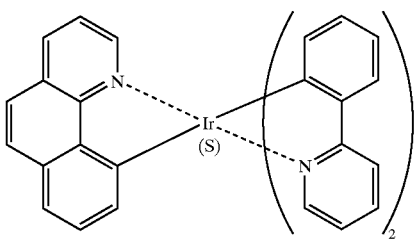

EXAMPLE 2

Tetrakis(benzo[h]quinoline-$C^2$,N')diiridium $(IrBzQ_2Cl)_2$ (structure shown below) was synthesized in a similar way as described above for $(IrPPy_2Cl)_2$ using 7,8-benzoquinoline in place of 2-phenylpyridine.

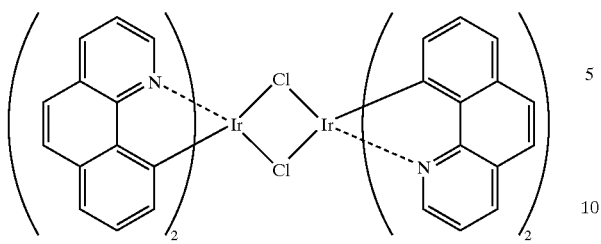

Iridium(III) bis(benzoquinolinato-N,C$^2$)acetylacetonate (structure shown below) was synthesized in a similar way as described for the corresponding acetylacetonate in Example 1 using (IrBzQ$_2$Cl$_2$)$_2$ in place of (IrPPy$_2$Cl)$_2$.

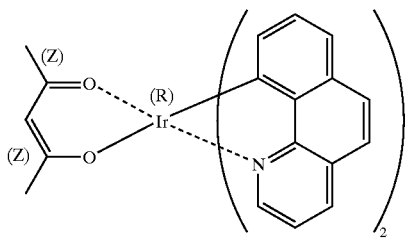

As described above in connection with Example 1, using iridium(III) bis(benzoquinolinato-N,C$^2$)acetylacetonate and 2-phenylpyridine, Iridium(III) bis(benzoquinolinato-N,C$^2$) 2-phenylpyridine was formed and found to have Td (5% weight loss) equal to 380° C. and yellow emission at 544 nm.

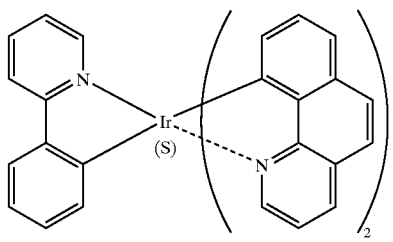

EXAMPLE 3

A compound of general formula (III) above may be synthesized according to the following reaction scheme:

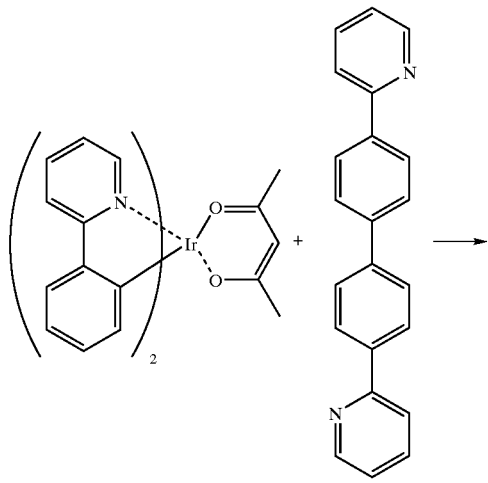

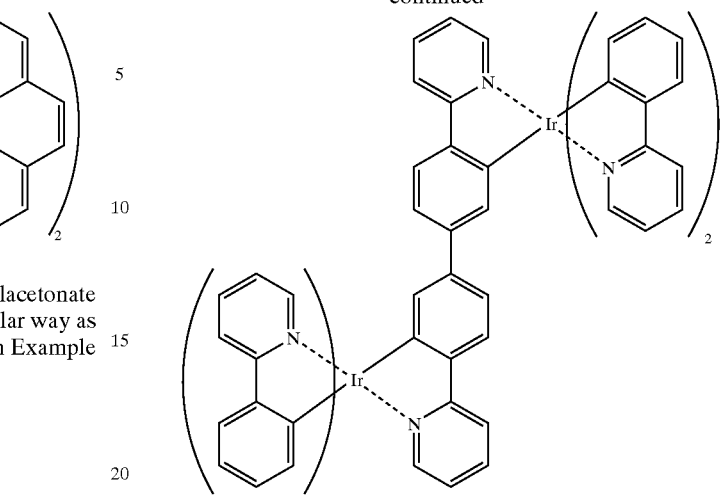

To a round-flask are added iridium(III) bis(2-phenylpyridinato-N,C$^2$)acetylacetonate (2 mole equivalent), 4,4'-pyridine-biphenyl (1 mole equivalent) and 10 mL of glycerol. The mixture is fluxed under N$_2$ overnight. After cooling down, water and CH$_2$Cl$_2$ are added to the mixture. The product is extracted with CH$_2$Cl$_2$, washed with water and purified by chromatography as described in the previous examples.

FIG. 1 schematically depicts a device according to the invention, including transparent substrate 1, anode 2 adjacent the substrate, hole transport layer 3 adjacent the anode, emissive layer 4 based on an iridium complex, electron transport layer/hole blocking layer 5, electron transport layer 6, and cathode 7. Each of these layers may itself comprise multiple layers of material having similar composition or function.

Devices according to the invention find use in display applications such as television screens, computer screens and image bar components for digital copiers and printers.

Suitable materials for substrate 1 include glass, quartz and the like, and polymers (including, without limitation, polyesters, polycarbonates, polyacrylates, polymethacrylates, and polysulfones). The thickness of the substrate is not critical and can range, for example, from about 25 to over 1,000 microns, depending on the structural demands of the device.

The anode 2 adjacent the substrate can be comprised of a metal, an alloy, an electroconducting compound, or mixtures thereof, especially with a work function equal to, or greater than about 4 electron volts. Specific examples of anodes include positive charge injecting electrodes such as indium tin oxide (ITO), tin oxide, zinc oxide, gold, platinum, electrically conductive carbon, and conjugated polymers such as polyaniline, polypyrrole, and the like. ITO is preferred. The thickness of the anode can range anywhere from about 10 nanometers to 1 micron.

The hole injecting layer 3 (also sometimes referred to herein as a hole transport layer) may be comprised of one layer comprising one, two or more hole transport components known in the art. Any conventional known materials which can inject and transport holes into the emissive layer may be employed for forming the hole injecting layer. Preferred hole injecting and hole transporting materials include porphyrin derivatives and aromatic tertiary amines, examples of which are disclosed in U.S. Pat. No. 4,720,432, the disclosure of which is incorporated herein by reference. N,N'-dinaphthyl-N,N'diphenyl-1,1'-biphenyl-4,4'diamine is a particularly preferred hole transporting layer.

The emissive layer 4 based on iridium complex may be doped in a host material or deposited neat. Suitable host materials include molecules including a carbazole moiety. A particularly preferred host material is 4,4'-N,N'-dicarbazole-biphenyl (CBP), having the following structure:

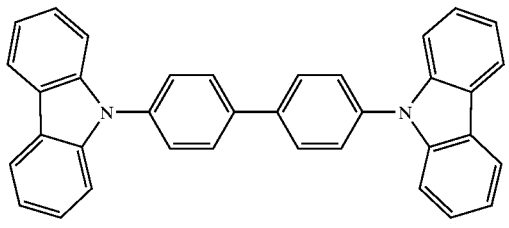

CBP: 4,4'-bicarbazolyl-biphenyl

In particularly preferred embodiments, the iridium complexes can be spin-coated neat onto a substrate.

Electron transport/hole blocking layer 5 has a band gap energy greater than the energy of excitons produced in the emission layer such that excitons cannot exist in the blocking layer, and has electron affinity to allow for transport of electrons. A suitable material for electron transport/hole blocking layer is 4,7-diphenyl-1,10-phenanthrolin (BCP) having the following structure:

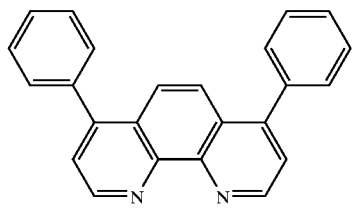

BCP: 4,7" diphenyl-1,10-phenanthroline

As an electron transport layer any known electron transport materials can be used. AlQ type materials, such as tris-(8-hydroxyquinoline)aluminum and derivatives thereof are particularly preferred. As noted above, electron transport capability can be incorporated into the emissive layer. Thus, the electron transport layer 5 is optional In embodiments of the present invention, the total thickness of the combined emissive, hole transport, electron transport and electron transport/hole blocking layers is less than about 1 micron, and preferably is from about 400 angstroms to about 4000 angstroms, sufficient to maintain a current density that permits efficient light emission under a relatively low voltage applied across the electrodes. Suitable thickness of the layers can range preferably from about 50 to about 2,000 angstroms, and preferably from about 400 to 1,000 angstroms. Driving voltages for devices according to the invention are preferably less than 20 V.

The cathode 6 can be comprised of any metal, including high or low work function metals. Aluminum, lithium, magnesium and calcium are particularly preferred.

Referring again to the reference numerals of FIG. 1, an OLED according to the invention may be made by first cleaning a glass substrate 1 having an ITO anode 2 patterned thereon in isopropyl alcohol for 5 minutes, followed by rinsing in deionized water for 5 minutes and in isopropyl alcohol again for an additional 5 minutes. The cleaned ITO substrate is placed in a substrate holder of a vacuum deposition chamber and the pressure is reduced to $2 \times 10^{-6}$ Pa. A layer of NPB having is deposited as a hole injection layer 3 by vacuum deposition to a thickness of 20 nm. An emissive layer 4, comprising 7 percent by weight of an iridium complex in a CBP host is deposited to a thickness of about 40 nm, also by vacuum deposition. An electron transport/hole blocking layer 5 of BCP is deposited to a thickness of 10 nm, followed by electron transport layer 6 AlQ₃ to a thickness of 20 nm. Finally, a bilayer cathode 7 is applied comprising a thin layer of LiF (0.8 nm) followed by Al (200 nm). A driving voltage is applied and a pure color emission is observed.

The foregoing examples are illustrative only and are not to be deemed limiting of the invention, which is defined by the following claims and is understood to include such obvious variations and modifications as would be obvious to those of ordinary skill in the art.

What is claimed is:

1. An emissive iridium (III) complex suitable for use in an emissive layer of an OLED, having the formula:

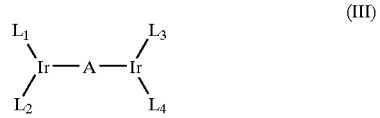

(III)

wherein A is a group L'-R-L" in which R is a divalent hydrocarbon radical, and L', L", $L_1$, $L_2$, $L_3$ and $L_4$ are heteroaromatic ligands having a carbon atom covalently bonded to the iridium atom and a nitrogen atom complexed to the iridium atom, wherein $L_1$, $L_2$, $L_3$ and $L_4$ are the same and not the same as L' or L".

2. An emissive iridium (III) complex suitable for use in an emissive layer of an OLED, having the formula:

(III)

wherein $L_1$, $L_2$, $L_3$ and $L_4$, which may be the same or different, are heteroaromatic ligands having a carbon atom covalently bonded to the iridium atom and a nitrogen atom complexed to the iridium atom, and wherein A is selected from the group consisting of:

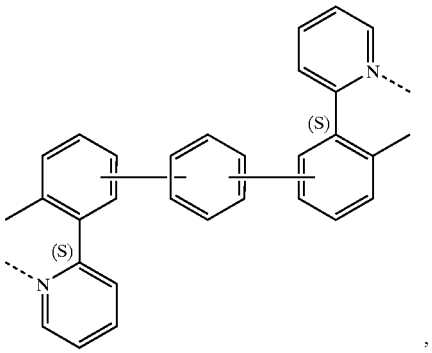

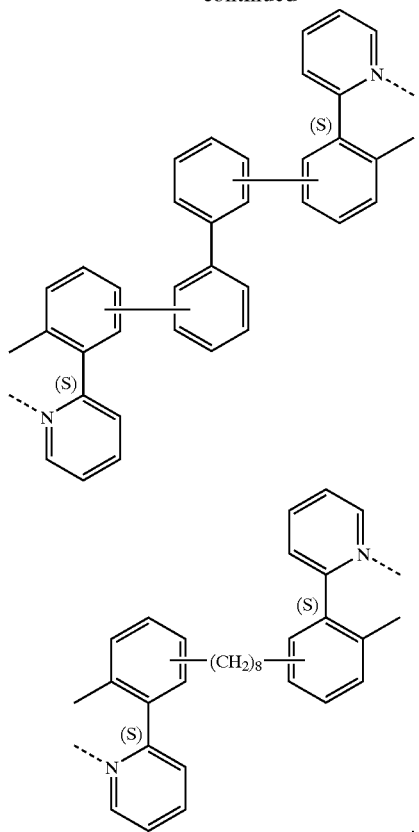

, and

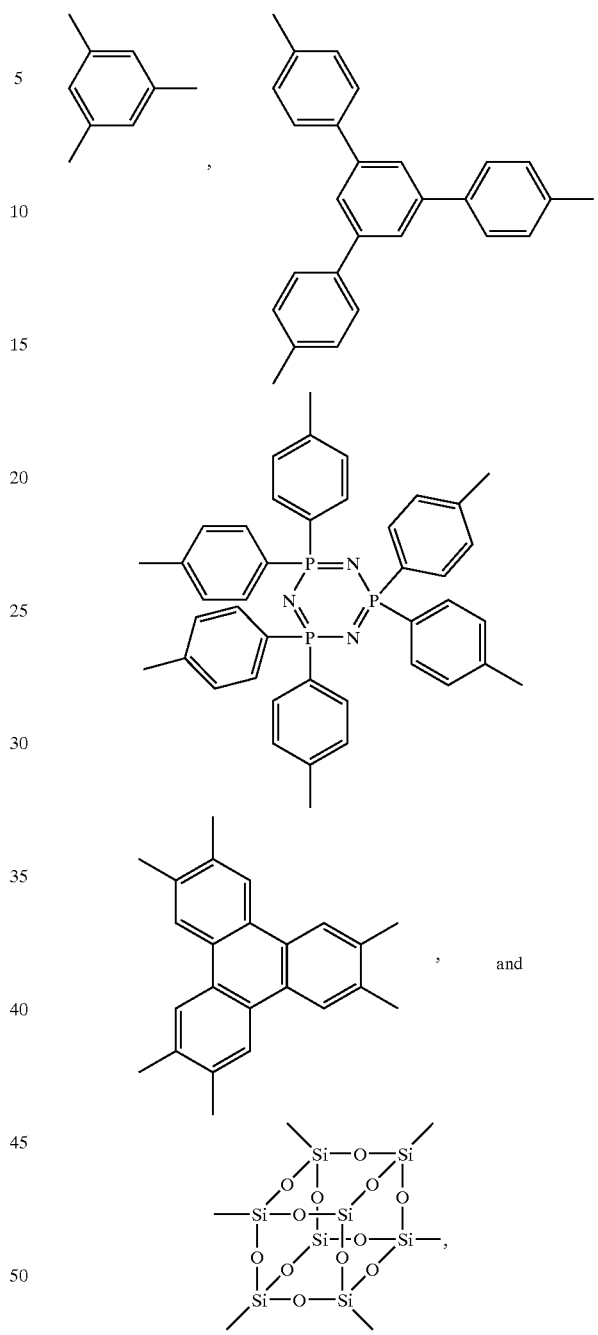

, and

3. An organic light emitting device comprising an anode, a cathode and an emissive layer, wherein the emissive layer comprises the emissive iridium (III) complex of claim 1 or claim 2.

4. The organic light emitting device of claim 3, wherein said complex is doped in a host material in said emissive layer.

5. The organic light emitting device of claim 3, wherein said complex is not doped in a host material.

6. The organic light emitting device of claim 3, having a theoretical efficiency greater than 25 percent.

7. An emissive iridium(III) complex suitable for use in an emissive layer of an OLED, having the structure $$\text{Core-R}_n\text{—L}'_n\text{—}\left(\text{Ir}\begin{pmatrix}L\\L\end{pmatrix}_m\right) \quad (IV)$$

wherein each Rn is a divalent hydrocarbon radical, L'n is a ligand having a carbon covalently bonded to the iridium atom and a nitrogen atom complexed to the respective iridium atom, and each ligand L, which may be the same or different, has a carbon atom covalently bonded to the iridium atom and a nitrogen atom complexed to the respective iridium atom, and wherein Core is selected from the group consisting of:

where n is 3–12, and
m is an integer equal to the valence of Core.

8. An organic light emitting device comprising an anode, a cathode, an electron transport layer, a hole transport layer, an electron transport/hole blocking layer, and an emissive layer comprising an iridium (III) complex according to claim 7.

9. The organic light emitting device of claim 8 having a theoretical device efficiency greater than 25 percent.

* * * * *